United States Patent
Yiu et al.

(10) Patent No.: US 11,779,300 B2
(45) Date of Patent: Oct. 10, 2023

(54) METHOD AND APPARATUS FOR DETECTING FLOW INSTABILITY

(71) Applicant: BIOPROBER CORPORATION, Bellevue, WA (US)

(72) Inventors: Yat Shun Yiu, Waterloo (CA); Adrian Jian Yuan Chee, Waterloo (CA); Alfred Cheuk Hang Yu, Kitchener (CA); Guo Tang, Bellevue, WA (US); Wenbo Luo, Bellevue, WA (US)

(73) Assignee: BIOPROBER CORPORATION, Bellevue, WA (US)

( * ) Notice: Subject to any disclaimer, the term of this patent is extended or adjusted under 35 U.S.C. 154(b) by 1017 days.

(21) Appl. No.: 16/563,125

(22) Filed: Sep. 6, 2019

(65) Prior Publication Data
US 2020/0077972 A1    Mar. 12, 2020

Related U.S. Application Data

(60) Provisional application No. 62/728,271, filed on Sep. 7, 2018.

(51) Int. Cl.
*A61B 8/00* (2006.01)
*A61B 8/06* (2006.01)
*A61B 8/14* (2006.01)
*A61B 8/08* (2006.01)

(52) U.S. Cl.
CPC ............. *A61B 8/06* (2013.01); *A61B 8/14* (2013.01); *A61B 8/483* (2013.01); *A61B 8/488* (2013.01); *A61B 8/5246* (2013.01); *A61B 8/5269* (2013.01)

(58) Field of Classification Search
CPC .. A61B 8/06; A61B 8/14; A61B 8/483; A61B 8/488; A61B 8/5223; A61B 8/5246; A61B 8/5269
See application file for complete search history.

(56) References Cited

U.S. PATENT DOCUMENTS

2009/0012398 A1* 1/2009 Zhang ................. G01S 7/52077
600/453
2009/0030319 A1* 1/2009 Zhang .................... A61B 8/488
600/454

(Continued)

OTHER PUBLICATIONS

Smith et al. "Maximum-Entropy and Bayesian Methods in Inverse Problems", pp. 419-420 (Year: 1985).*

(Continued)

*Primary Examiner* — Christopher L Cook
(74) *Attorney, Agent, or Firm* — HAUPTMAN HAM, LLP

(57) ABSTRACT

A method of detecting flow instability includes insonating an area of interest with ultrasound wave pulses, acquiring radio frequency (RF) data from echo pulses of the ultrasound wave pulses, processing the RF data, and deriving a Doppler band-width from the processed RF data by AR modeling. Also described herein is a device for detecting flow instability. The device includes an emitter configured to insonate ultrasound wave pulses on an area of interest, a receiver configured to acquiring radio frequency (RF) data from echo pulses of the ultrasound wave pulses, and a processor configured to process the RF data, and derive a Doppler band-width from the processed RF data by AR modeling.

19 Claims, 9 Drawing Sheets

(56) References Cited

U.S. PATENT DOCUMENTS

| | | | | |
|---|---|---|---|---|
| 2010/0286522 A1* | 11/2010 | Beach | .................. | A61B 8/08 |
| | | | | 600/441 |
| 2015/0141832 A1* | 5/2015 | Yu | ........................ | G06T 7/20 |
| | | | | 600/455 |
| 2017/0273699 A1 | 9/2017 | Bailey et al. | | |

OTHER PUBLICATIONS

Yiu et al., "High frame rate doppler ultrasound bandwidth imaging for flow instability mapping", Medical Physics, 46 (4), Apr. 2019, pp. 1620-1633.
Search Report issued in corresponding European Patent Application No. 19857368.5; dated May 10, 2022; 9 pgs.
Cloutier, Guy et al.: "Performance of Time-Frequency Representation Techniques to Measure Blood Flow Turbulence With Pulsed-Wave Doppler Ultrasound", Ultrasound in Med. & Biol., vol. 27, No. 4, 2001, pp. 535-550.
Guo, Z et al., "Cardiac Doppler blood-flow signal analysis Part 2 Time/frequency representation based on autoregressive modeling"; Medical & Biological Engineering & Computing, 31; Publication [online]. Published May 1993 [retrieved Nov. 11, 2019]. Retrieved from the Internet: <URL: https://www.ncbi.nlm.nih.gov/pubmed/8412377>;<DOI: 10.1007/bf02458043>.
International Search Report and Written Opinion dated Nov. 16, 2019 from corresponding application No. PCT/US19/50026.

\* cited by examiner

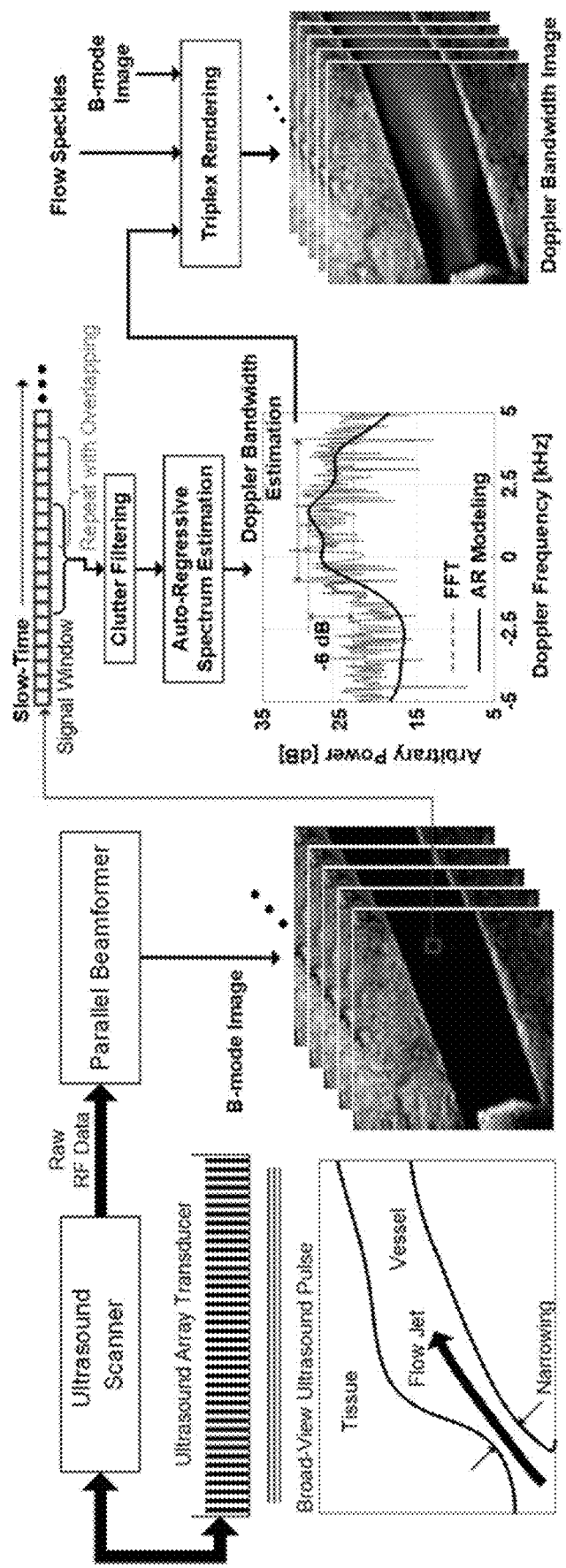

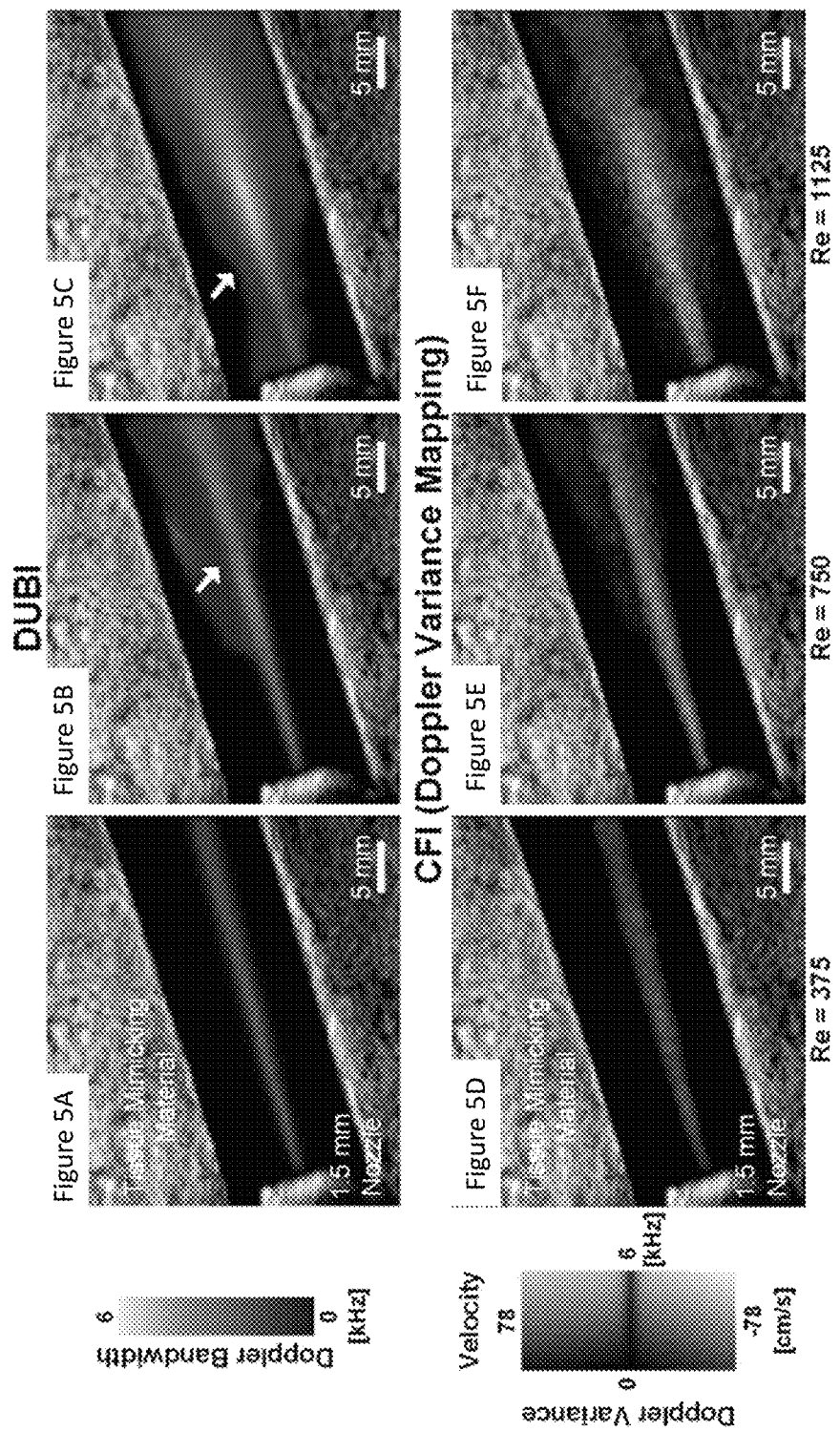

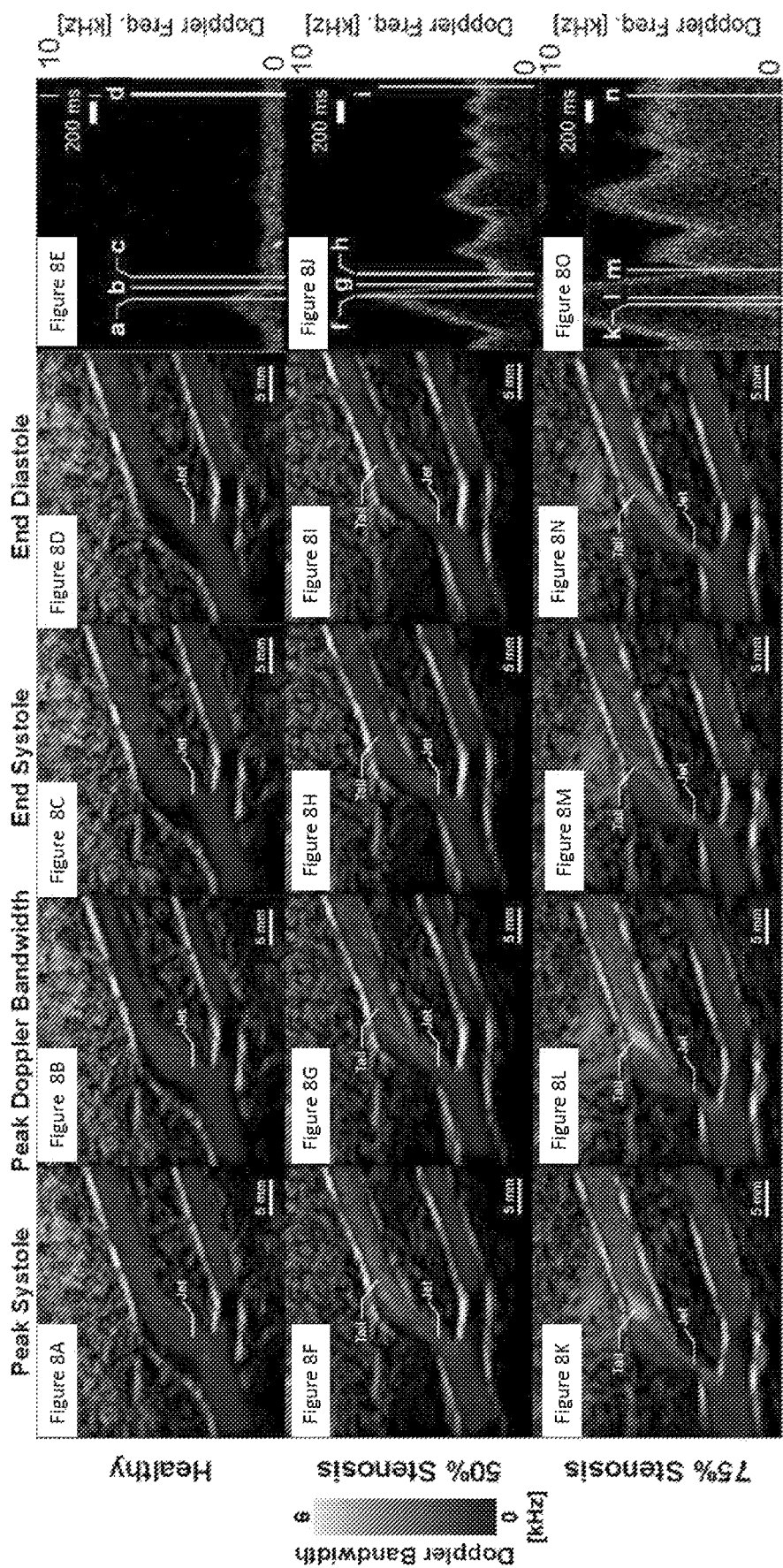

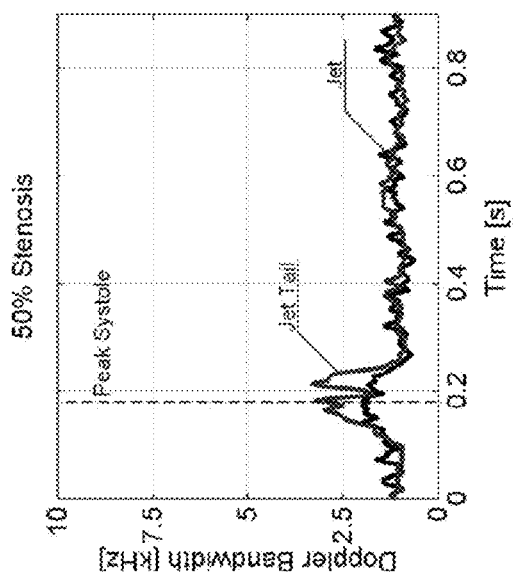 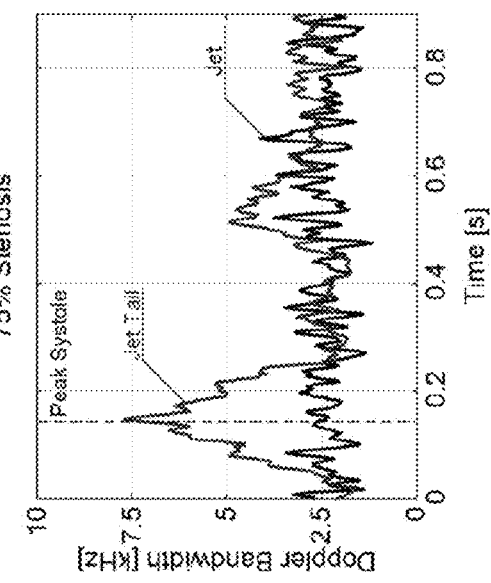
Figure 9A
Figure 9B

METHOD AND APPARATUS FOR DETECTING FLOW INSTABILITY

PRIORITY CLAIM AND CROSS-REFERENCE

The application claims priority from U.S. provisional Application No. 62/728,271 filed on Sep. 7, 2018, the entirety of which is hereby incorporated herein by reference.

BACKGROUND

Flow instability, such as flow instability in blood vessels due to narrowing of the blood vessels, has been shown to contribute to the risk of, among others, future cardiovascular and cerebrovascular events in humans and animals. Nonetheless, noninvasively detecting and identifying flow instability in blood vessels is challenging.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIGS. 3A, 3B and 3C are diagrams of a method detecting flow instability in accordance with some embodiments.

FIGS. 5A-5C are images of a detected flow instability in accordance with some embodiments with a contrast enhanced ultrasound (CEUS) method.

FIGS. 5D-5F are images of a detected flow instability in accordance with some embodiments with a CFI (Doppler Variance Mapping) method.

FIGS. 8A-8O are images of results of a method of detecting flow instability in accordance with some embodiments.

FIGS. 9A-9B are images of a Doppler bandwidth of a stenosis model in accordance with some embodiments.

DETAILED DESCRIPTION

Figure 1:
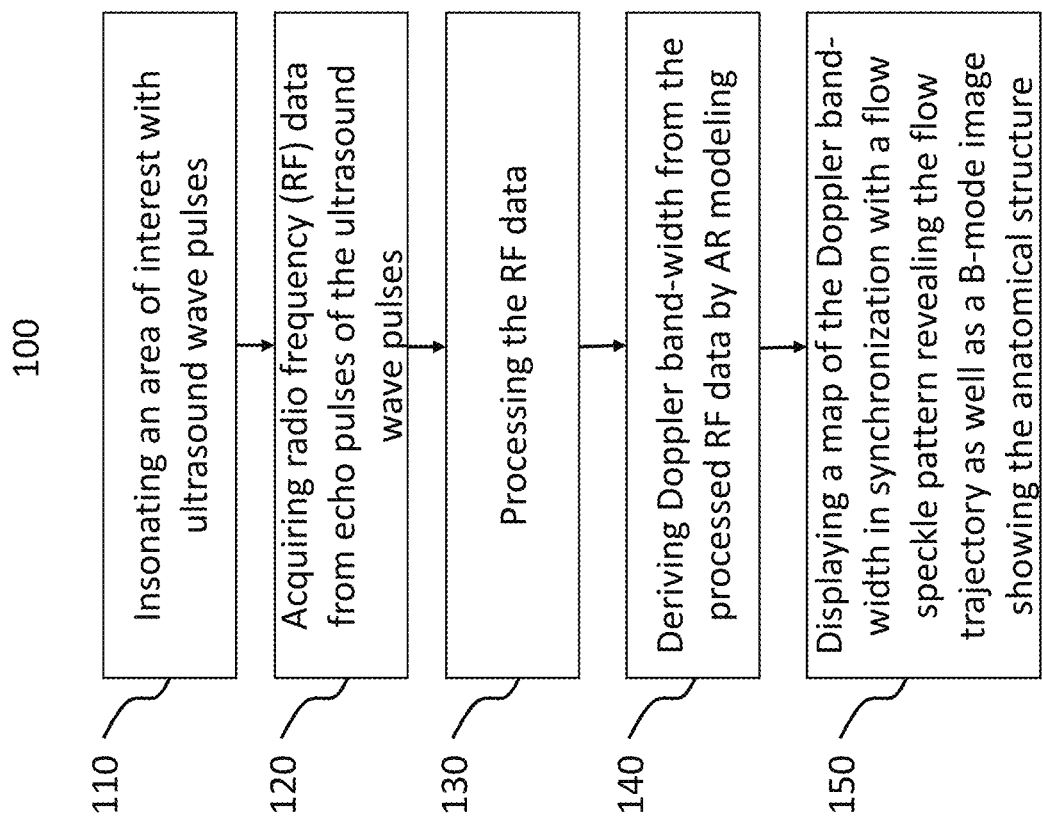
FIG. 1 is a flowchart of a method of detecting flow instability in accordance with some embodiments.
Figure 2:
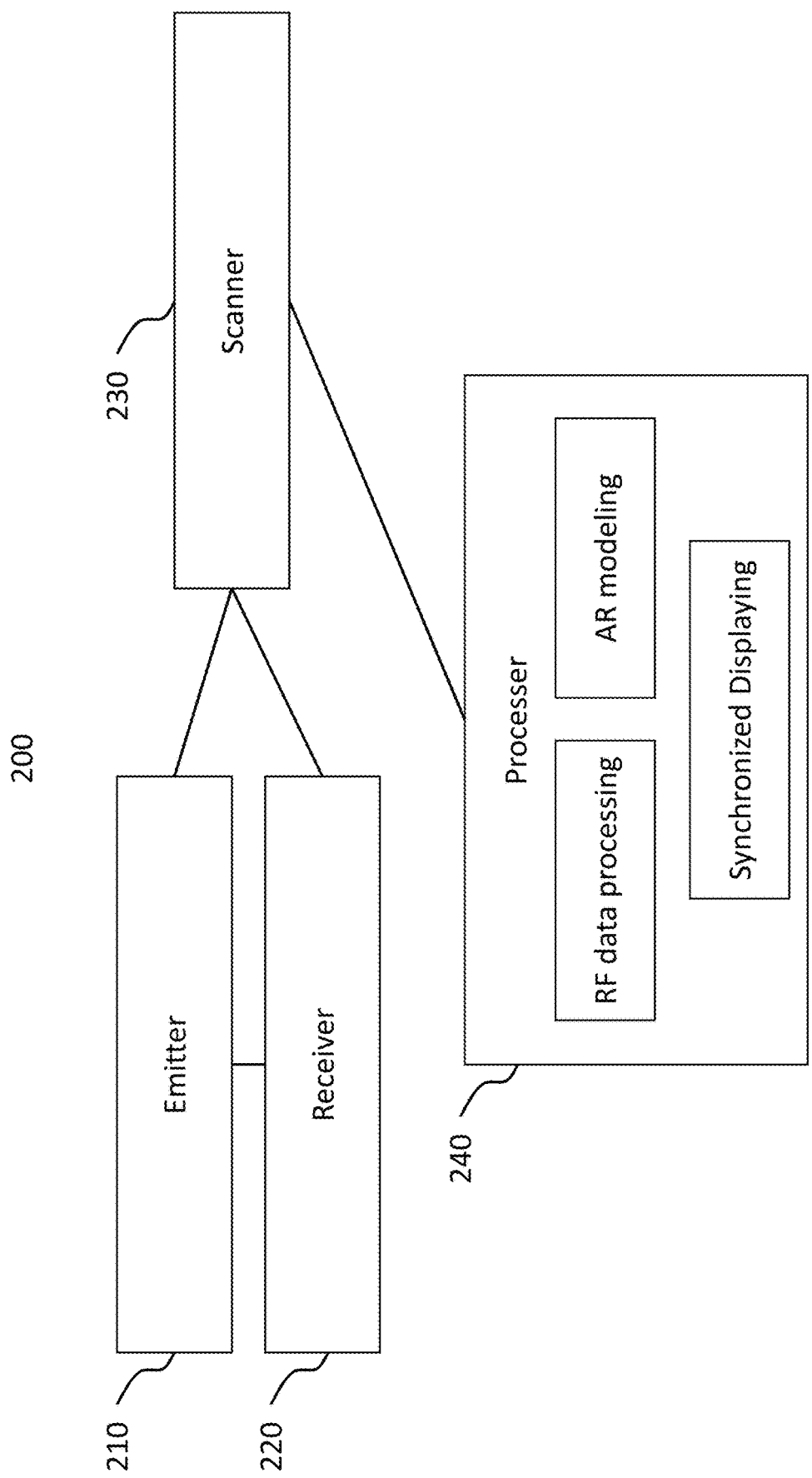
FIG. 2 is a schematic diagram of a device for detecting flow instability in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not necessarily dictate a relationship between the various embodiments and/or configurations discussed.

Method of Detecting Flow Instability

In some embodiment, the disclosure is directed to a method of detecting flow instability.

In some embodiment, the disclosure is directed to a method of detecting flow instability in blood vessels of humans or animals. In some embodiments, disclosure is directed to a method of detecting flow instability in blood vessels caused by narrowing of the blood vessels.

Flow instability is caused by the narrowing of blood vessels (vascular stenosis), in some instances. An example of vascular stenosis is the carotid atherosclerotic stenosis, the narrowing of the carotid arteries, major blood vessels in the neck that supply blood to the brain, neck, and face. Carotid atherosclerotic stenosis can cause stroke or stroke-like attack.

Risk stratification of carotid atherosclerotic stenosis in other approaches is based on measurements of luminal narrowing and peak systolic velocity. However, atherosclerotic plaques with identical degree of stenosis could have substantial differences in their associated risk, thereby prompting for diagnostic considerations beyond the immediate stenotic site. From a hemodynamics standpoint, the presence of stenosis perturbs blood flow, and in turn the stenosis could lead to flow instability. This phenomenon forms the underlying basis for physical examinations of carotid atherosclerosis via the detection of carotid bruit using a stethoscope. Unstable blood flow (i.e., nonlaminar flow, including turbulence) has also been associated with atherogenesis and plaque progression, as well as an increased risk for thrombosis and embolization. Thus, monitoring blood flow instability could offer new clinical insights to understand the mechanism of atherosclerotic plaque development, as well.

Instability of flow is characterized by the fluctuations of flow velocities in space and time. Medical imaging modalities have been leveraged to derive the flow turbulence index, a parameter describing the variance in flow velocities at specific cardiac instances between multiple consecutive cardiac cycles. For example, phase-contrast magnetic resonance imaging has demonstrated feasibility in mapping turbulent flow regions from measurements of intra-voxel mean velocity variations. Similarly, Doppler ultrasound is usable to calculate the turbulence index by measuring the standard deviation of flow velocities over successive cardiac cycles. However, fluctuations in heart rate and stroke volume pose a significant drawback for the turbulence index approach due to its susceptibility to intercardiac-cycle variations.

Instead of relying on measurements over multiple cardiac cycles, detecting unstable flow is possible by identifying high-frequency velocity fluctuations at specific instants in a cardiac cycle. In some approaches, instantaneous blood velocity fluctuation is measured using an intravascular catheter, but this approach is highly invasive. In some approaches, Doppler ultrasound has been used to noninvasively detect flow instability in the form of Doppler spectral broadening (as an effect of flow velocity fluctuations) based on the characterization of Doppler spectral bandwidth. This approach has demonstrated initial success in assessing plaque risk. Yet, Doppler ultrasound, which only operates on a single range gate, lacks the ability to track fluctuations in flow velocities in multiple spatial positions.

A workaround of Doppler ultrasound's single-gate data acquisition paradigm is to perform Doppler-based color flow imaging (CFI) that can provide color-coded rendering of mean axial velocity estimates or velocity variance estimates. With CFI, which is a full-view version of single-gate Doppler ultrasound, unstable flow regions are able to be visually identified as puff-like color patches or mosaic color patterns in the CFI frame. Nevertheless, there are multiple caveats in using CFI for flow instability analysis. First, although CFI yields real-time frame rates within the video display range (~20 fps), time resolution of CFI has difficulty following the fast-changing nature of unstable flow, in some instances. Second, CFI data acquisition involves multiple firings over each of the scanlines in the image view, so each CFI frame is not able to capture a coherent spatial snapshot of unstable flow. Third, CFI's derivation of flow estimate at a pixel position is prone to significant fluctuations and inaccuracies because each slow-time ensemble used for Doppler processing is limited in size (8-16 samples) as constrained by real-time requirements. Given all these issues, a risk that puff-like or mosaic coloring patterns in a CFI frame are simply spurious artifacts rather than true indications of unstable flow, especially if CFI parameters are not tuned properly, is high.

In some embodiments, the method of detecting flow instability 100 includes: insonating an area of interest with ultrasound wave pulses 110; acquiring radio frequency (RF) data from echo pulses of the ultrasound wave pulses 120; processing the RF data 130; and deriving a Doppler bandwidth from the processed RF data by AR modeling 140.

In some embodiments, insonating the area of interest with the ultrasound wave pluses 110 includes insonating the area of interest with an unfocused plane wave, a diverging spherical wave, a weakly focused wide beam wave or a focused converging wave. In some embodiments, the insonation of the area of interest includes a broad-view insonation. In some embodiments, the ultrasound wave is a high-frame-rate ultrasound wave.

In some embodiments, acquiring RF data 120 includes acquiring RF data from each array channel of a plurality of array channels.

In some embodiments, processing the RF data 130 includes beamforming the RF data to generate a full-view image of the area of interest. In some embodiments, performing beamforming of the echo data includes performing parallel beamforming.

In some embodiments, processing the RF data 130 further includes forming a 3D data matrix by stacking a plurality of the full-view images along a slow-time dimension; and applying clutter filtering to the 3D data matrix. In some embodiments, processing the RF data 130 further includes applying clutter filtering to the 3D data matrix.

In some embodiments, the method of detecting flow instability 100 is a method of detecting flow instability in a blood vessel. In some embodiments, the blood vessel is an artery.

In some embodiments, the insonating an area of interest with ultrasound wave pulses 110, acquiring radio frequency (RF) data from echo pulses of the ultrasound wave pulses 120, and processing the RF data 130 are repeated at different phases of cardia cycle to capture temporal information over the different phases of cardia cycle.

In some embodiments, deriving Doppler band-width of the processed RF data by AR modeling 140 includes estimating the Doppler band-width at a given pixel position over a short period by first deriving an AR model of the slow-time ensemble and then estimate the signal model's spectral power. In some embodiments, the Doppler bandwidth is determined as the full-width at half maximum (FWHM) of the power spectrum. In some embodiments, the estimation of the Doppler band-width process is repeated for every image pixel to generate a Doppler ultrasound bandwidth imaging (DUBI) frame as a depiction of flow instability over the image view. In some embodiments, to track the evolution of Doppler bandwidth over time, the entire estimation procedure is repeated at subsequent time points (M slow-time samples apart) to generate a time series of DUBI frames over the image view (see FIG. 3B).

In some embodiments, deriving Doppler band-width of the processed RF data by AR modeling 140 includes modeling an $n^{th}$ sample in a slow-time ensemble with N samples according to a $P^{th}$-order complex AR model representation according to the following Equation 1:

$$x[n] = -\sum_{k=1}^{P} a_{P,k} x[n-k] + e[n] \qquad \text{<Equation 1>}$$

wherein in Equation 1, $a_{P,k}$ is the $k^{th}$ complex AR parameter of the model, and e[n] is the nth sample in the complex modeling error.

In some embodiments, the set of AR parameters $\{a_{P,k}\}$ are iteratively estimated using Burg's method to yield good spectral estimation reliability, since Burg's method works by iteratively minimizing the mean of forward and backward prediction errors.

In some embodiments, deriving Doppler band-width of the processed RF data by AR modeling 140 further comprises calculating Doppler power spectrum $S_{AR}[f]$ for the ensemble x[n] is constructed from the AR model through parametric spectral fitting as defined by the following Equation 2:

$$S_{AR}[f] = \frac{\sigma_p^2 \Delta t}{\left|1 + \sum_{k=1}^{P} a_{P,k} e^{-j2\pi f k \Delta t}\right|^2} \qquad \text{<Equation 2>}$$

wherein, in Equation 2, f is the bin frequency, $\Delta t$ is the pulse repetition interval and $\sigma_p^2$ is an average of mean powers of forward and backward prediction errors.

Referring to FIG. 3B, in some embodiments, the Doppler bandwidth of the slow-time ensemble is determined as the full-width at half maximum (FWHM) $S_{AR}[f]$, after normalizing $S_{AR}[f]$ to the maximum power of $S_{AR}[f]$.

Deriving a Doppler band-width from the processed RF data by AR modeling is desirable because through the use of AR modeling, DUBI's Doppler bandwidth estimation process became a task of finding the FWHM over a smoothened Doppler power spectrum. In turn, DUBI's Doppler bandwidth estimation process is less susceptible to random spectral spikes that might arise in Doppler power spectra derived from the classical periodogram approach, thereby improving the consistency of Doppler bandwidth estimates in comparison with other approaches. Another advantage of deriving the Doppler power spectrum using an AR modeling approach is that the spectrum could be reconstructed with a finer spectral resolution and not be bounded by the number of samples in the slow-time signal. In doing so, the resulting Doppler bandwidth estimates were more accurate as they were less prone to discretization noise.

Without wishing to be bound by theories, the inventors believe that flow instability naturally gives rise to a wide range of flow velocities over a sample volume in the area of interest. Since the flow velocity correlates with the magnitude of the Doppler shift, the wide range of flow velocities would in turn yield a larger Doppler bandwidth estimate.

Therefore, in some embodiments, flow instability is determined to exist when the derived Doppler band-width is equal to or larger than the predetermined value. In some embodiments, flow instability is determined to not exist when the derived Doppler band-width is smaller than the predetermined value.

In some embodiments, samples of RF data used in deriving the Doppler band-width are samples from a time window having a duration significantly shorter than a duration of a cardiac cycle.

Since a cardiac cycle has a duration of about 0.6-1 second in humans, in some embodiments, the duration of insonation is 100 milliseconds (ms) or less, such as 50 ms or less, 40 ms or less, 30 ms or less, 20 ms or less, 10 ms or less, 5 ms or less, 2 ms or less, or 1 ms or less. If the duration of insonation is larger than 100 ms, the flow velocity variation caused by the changes of the cardiac cycle phases could introduce noise.

In some embodiments, the method of detecting flow instability further includes comparing the derived Doppler band-width with a predetermined value. In some embodiments, comparing the derived Doppler band-width with a predetermined value includes comparing the derived Doppler band-width at one or more pixels of a full-view image with a predetermined value.

In some embodiments, the method of detecting flow instability 100 further includes displaying a map of the Doppler band-width in synchronize with a flow speckle pattern revealing the flow trajectory or a B-mode image 150.

With the derived Doppler bandwidth estimates at every pixel position over different time instants, DUBI frames are able to be formed as a triplex display scheme to facilitate visualization of flow instability in an image view over time. As shown in FIG. 3C, DUBI is able to be synchronously display: (a) the Doppler bandwidth map annotating the flow instability of each pixel location; (b) flow speckle pattern revealing the flow trajectory; and/or (c) B-mode image showing the anatomical structure.

Flow speckle co-visualization is able to be performed by color-encoded speckle imaging, in which flow speckle values were derived at different pixel positions by calculating the power of the corresponding slow-time ensemble after clutter filtering. Descriptions of flow speckle co-visualization are found in the article "High-frame-rate ultrasound color-encoded speckle imaging of complex flow dynamics" published on Ultrasound Med Biol. by the instant inventors, the entirety of which is hereby incorporated herein by reference.

In some embodiments, to form DUBI's triplex display, the flow speckle map is first overlaid on top of the B-mode image at flow regions and displayed as the base layer. Then, the Doppler bandwidth estimates are mapped to a thermal hue with brighter colors corresponding to higher Doppler bandwidths. This color map is subsequently overlaid using alpha compositing principles. For nonflow region, transparency is set to 100% to reveal the anatomical structure. For flow regions, the transparency is set to 70% to reveal the flow speckle pattern and the color-coded Doppler bandwidth estimates. This rendering strategy is repeated over different time points, and the image frames were stacked together to form a cineloop.

Device for Detecting Flow Instability

In some embodiments, the disclosure is directed to a device for detecting flow instability 200. The device for detecting flow instability 200 includes: an emitter 210 configured to insonate ultrasound wave pulses on an area of interest; a receiver 220 configured receive echo pulses of the ultrasound wave pulses; a scanner 230 configured to acquiring radio frequency (RF) data from the echo pulses; and a processor 240 configured to: process the RF data; and derive a Doppler band-width from the processed RF data by AR modeling.

In some embodiments, the emitter 210 or the receiver 220 includes an ultrasound array transducer.

In some embodiments, the processor 240 is configured to process the RF data or derive the Doppler band-width from the processed RF data by AR modeling in manners similar to those as described in the previous section.

In some embodiments, the processor 240 is further configured to generate a flow speckle pattern revealing the flow trajectory or a B-mode image using the RF data acquired by the receiver.

In some embodiments, the processor 240 is further configured to generate a map of the Doppler band-width in synchronize with the flow speckle pattern or the B-mode image to be displayed by a display. In some embodiments, the processor 240 is configured to generate the map of the Doppler band-width based on synchronization with the flow speckle pattern or the B-mode image in manners similar to those as described in the previous section. In some embodiments, a display is included in device 200. In some embodiments, device 200 is configured to be connected to an external display.

In some embodiments, the processor 240 is further configured to compare the Doppler band-width with a predetermined value. In some embodiments, a Doppler band-width equal to or larger than the predetermined value indicates flow instability, and a Doppler band-width smaller than the predetermined value indicates a stable flow.

EXAMPLES

Example 1: Implementation Methods of DUBI

Example 1-1: Imaging Hardware and Data Acquisition

DUBI was implemented on a programmable research platform that was built upon ultrasound flow imaging innovations described in the articles "High-frame-rate ultrasound color-encoded speckle imaging of complex flow dynamics" and "Vector Projectile image: time-resolved dynamic visualization of complex flow pattern" published by the instant inventors. Both of the articles are hereby incorporated herein in their entireties by reference. The platform consisted of a 128-channel programmable transmit frontend (SonixTouch; Analogic Ultrasound, Peabody, MA, USA), a pre-beamformed DAQ tool with 40 MHz sampling rate and 12-bit resolution, 41 and a high-speed processing platform based on graphics processing unit (GPU) technology (GTX 1080; NVidia Corporation, Santa Clara, CA, USA) for beamforming and signal processing. Our research platform was programmed to perform high-frame-rate data acquisition as required. Broad-view acquisition at 10 kHz was achieved with unsteered plane wave excitation (0° transmission; 5

MHz center frequency, 5-cycle pulse) using an L14-5 linear array (0.3048 mm pitch; Analogic Ultrasound). Accordingly, raw data frames were acquired at a rate of 10,000 fps. Also, the transmit pulse shape yielded an effective axial range of 0.77 mm according to established formulas.49 In each acquisition, the raw channel-domain data were stored on the DAQ tool until the internal 16 GB memory buffer was filled (3 s duration at 5 cm imaging depth). The data were then streamed offline to the GPU platform for processing.

Example 1-2: Plane Wave Image Formation

For each frame of the acquired dataset, parallel beamforming was performed on the GPU computing platform using a codec programmed in Matlab (R2016a; Mathworks Inc., Natick, MA, USA) in which the GPU-accelerated parallel beamforming library was invoked. The codec first applied a 3-7 MHz bandpass filter to the received RF data on a per-channel basis to suppress out-of-band white noise. The filter was implemented as a finite-impulse-response (FIR) filter in Matlab, with minimum filter order (30 taps) formulated using the Parks-McClellan equiripple design algorithm. The analytic form of the acquired data was subsequently obtained using a FIR-based Hilbert transformer (50th order) as described earlier. With the analytic RF data, image frames (with 0.2 mm pixel spacing) were finally parallel beamformed using our GPU-based delay-and-sum algorithm (64 array channels were used with Hanning apodization). This three-stage process was repeated for the data of different slow-time sampling instants, thereby generating a stack of image frames over slow-time for Doppler signal processing and bandwidth estimation. Note that, for our 64-channel receive aperture configuration, the effective lateral width was estimated to range between 0.31 and 0.77 mm for a 2-5 cm imaging depth range, as determined based on well-known formulas. Also, with its apodization profile, our receive beamformer's maximum sidelobe magnitude (occurred at 2 cm depth) was found to be 27.6 dB lower than that for the main lobe, according to in-house point target simulations.

Example 1-3: Signal Processing for Doppler Bandwidth Estimation

Doppler bandwidth estimation was performed at various slow-time instants on a per pixel basis. First, a Doppler clutter filter was applied to suppress tissue echoes; this filter was implemented as a FIR high-pass filter with 0.05 normalized cutoff frequency (i.e., 250 Hz for 10 kHz slow-time sampling rate), and its filter order was optimized to be 135 taps using the equiripple filter design algorithm. For flow regions, Doppler bandwidth estimation was performed over each slow-time ensemble with N=100 samples, equivalent to windows of 10 ms observation period. This relatively short duration was chosen to limit spectral broadening induced by rapid acceleration (and deceleration) of blood flow. The corresponding AR-based Doppler spectrum was subsequently derived as described. For our implementation, an 8th-order AR model was chosen as its performance has been shown to be similar to higher order models (up to $16^{th}$ order) in earlier work.37 Also, the AR-modeled power spectrum was formed with a 10 Hz spectral resolution (i.e., 0.001 normalized frequency relative to slow-time sampling rate) to avoid spectral discretization noise.

To accelerate the derivation of each DUBI frame, Doppler bandwidth estimation for multiple pixels was executed concurrently by devising a GPU-based parallel computing kernel for AR modeling. This GPU kernel was implemented using the C++ programming language and the compute unified device architecture application programming interface (ver. 7.5; NVidia Corporation). Its formulation, as explained in the Appendix, was based on a public-domain computing algorithm for Burg's method. After completing the Doppler bandwidth estimation process for each DUBI frame, it was repeated at other slow-time sampling instants to generate a time series of Doppler bandwidth maps. In particular, a repetition was performed after shifting the observation window by 25 samples along slow-time (i.e., M=25; with 75% overlap for N=100). The effective frame rate of the Doppler bandwidth maps was 400 fps (10,000 fps raw data frame rate divided by 25). The resultant Doppler bandwidth maps were finally rendered as described previously.

Example 2: Experimental Testing Methods

Example 2-1: Nozzle-Based Unstable Flow Model

To evaluate the performance of DUBI in identifying unstable flow zones, a nozzle-flow setup was devised to generate flow conditions ranging from laminar to turbulent flow. The flow conditions were characterized by their Reynolds number Re, defined as Re=uD/m, where u is the average flow velocity, D is the nozzle diameter and m is the fluid kinematic viscosity. Since the average velocity term u is known to be equal to flow rate Q divided by cross-sectional area A (i.e., u=Q/A), the Reynolds number could be readily rewritten as Re=4Q/πDm. Based on this relation, we realized different values of Re by changing the flow rate. In turn, a series of flow conditions with progressing degree of flow disturbance was generated by increasing the flow rate. For each of these flow conditions, the stable and unstable flow regions were identified with the aid of CEUS (to be discussed in Example 2-3).

Figure 4B:
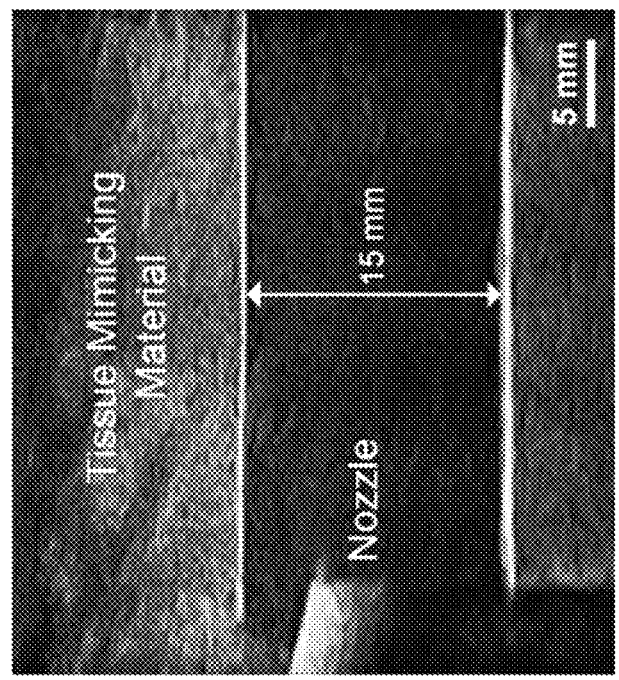
FIG. 4B is an image of a nozzle-based unstable flow model in accordance with some embodiments.
Figure 4A:
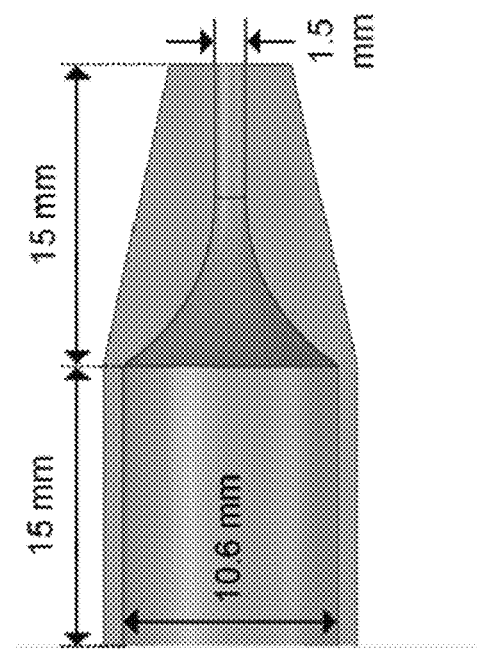
FIG. 4A is a side view of a nozzle in accordance with some embodiments.

In terms of the nozzle design, it was shaped as a curved funnel to progressively narrow the flow channel's diameter from 10.6 to 1.5 mm over a 15 mm passage [see FIG. 4A] which gradually increased the flow velocity. The model's base was elongated by 15 mm so that a flow connector (EW-06361-61; Cole-Parmer, Vernon Hills, IL, USA) could be securely affixed to the base end. The nozzle was then inserted into a phantom made of poly-vinyl alcohol (PVA) (fabrication details discussed in Example 2-2) for flow to be discharged into a 15 mm diameter straight tube flow channel. The phantom provided an acoustic window to image the discharged flow from the nozzle. Note that this nozzle-flow geometry serves as an idealized model of stenosis (with 90% reduction in diameter in this case).

Example 2-2: Fabrication of Nozzle-Flow Model and Flow Circuit Setup

3-D printing was leveraged to physically construct the nozzle. First, its physical dimensions were drafted on computer-aided design (CAD) software (SolidWorks; Dassault Systems, Waltham, MA, USA). To compile 3-D printing instructions, the CAD model (saved in STL stererolithography file format) was imported into a slicer software (KISSlicer; ver 1.5). The instructions were then downloaded to a fused deposition modeling (FDM) system (Model DX; CreatBot 3D Printer, ZhengZhou, China) with a nozzle size of 0.25 mm to create the physical models. Layer and skin thicknesses of 0.1 and 0.5 mm were used, respectively.

The flow phantom was fabricated based on investment casting principles according to the protocol reported in our previous work. In this study, a PVA-based wall-less flow phantom with a 15 mm diameter flow channel across a tissue mimicking slab was fabricated. The flow channel was formed by first embedding a straight rod in PVA solution and then removing the rod after the solution has congealed. The straight rod was 15 mm in diameter with a length of 280 mm, and it functioned as the negative replica of the flow channel. For the phantom to grip onto the inlet nozzle and outlet flow connector, 30 mm on both ends of the rod were narrowed to 9 mm diameter (effective length of the flow channel became 220 mm). Similar to the nozzle, the inner core was drafted on SolidWorks and was physically constructed using the FDM system with the same settings. Next, the rod was gently polished using an abrasive paper (400 grit size) and was suspended in the phantom case ($80\times295\times70$ mm$^3$, w$\times$l$\times$h) by mounting it onto two side plates. Tissue mimicking material was casted around the straight rod by: (a) pouring PVA solution into the phantom case, (b) administering three freeze-thaw cycles (freeze in $-20°$ C. for 24 h followed by thawing at 4° C. for 24 h).

Note that the PVA mixture consisted of 10% PVA (341584; Sigma-Aldrich, St Louis, MO, USA), 3% graphite (282863; Sigma-Aldrich), 0.3% potassium sorbate (85520; Sigma-Aldrich), and 86.7% distilled water. The acoustic attenuation and speed of this tissue mimicking material were respectively 0.229 dB/(cm·MHz) and 1535 m/s as reported earlier. Upon completing the thermal cycling process, the flow channel was instated by simply sliding the straight rod out from one end of the phantom.

After the flow phantom was fabricated, the nozzle was affixed into the inlet flow connector. The setup was then connected to a programmable flow pump (details described elsewhere) that fed blood mimicking fluid at constant flow rates according to the parameters listed in Table I to generate a range of flow conditions as discussed earlier. Note that the blood mimicking fluid was fabricated using an Orgasol-based standardized formula and a laboratory procedure that we have described previously. Its dynamic viscosity (4.1 mPa·s) and density (1037 kg/m$^3$) were matched to that for human blood. FIG. 4B shows a B-mode image of the inlet segment of the assembled flow phantom captured using a clinical scanner (SonixTouch; Analogic Ultrasound).

TABLE I

Flow rate and ROI sizes for each flow condition.

| Flow conditions in Reynolds number Re | Flow rate (ml/s) | ROI length (mm) | |
|---|---|---|---|
| | | Stable | Unstable |
| 375 | 1.8 | 34.1 | — |
| 750 | 3.5 | 18.2 | 8.4 |
| 1125 | 5.2 | 6.2 | 19.2 |

Example 2-3: Identification of Unstable Flow Region with CEUS

To facilitate the identification of regions with the presence of unstable flow, microbubble contrast agents were administered to trace flow trajectories. The rationale behind was that laminar flow occurs when fluid flows in parallel layers with no disruption between the layers. As such, microbubbles in stable regions would move in a straight path. On the contrary, unstable flow would correspond to cases where trajectories of the microbubbles were observed to have crossed each other's path. In accordance with this notion, a bolus of microbubble contrast agents (USphere Prime; Trust BioSonics, Hsinchu, Taiwan) were slowly injected manually to the inlet of the flow phantom for CEUS imaging.

Plane wave data acquisitions were repeated for all flow rates using the same data acquisition scheme described in Example 1-1, but with a 5 MHz, 2-cycle pulse at 50% of the original transmit power instead to excite the microbubbles in the stable cavitation regime. High-frame-rate CEUS images were then generated through the same image formation method described in Example 1-2. To highlight flow trajectories, high-persistence B-mode images were rendered by averaging the beamformed RF signal magnitude over multiple frames before log compression. This allowed the hyperechogenic microbubbles to create streaks along their trajectory, representing the flow path lines. This process was repeated every K frames with overlapping to generate a cineloop of flow path lines for analysis.

The image persistence and overlapping (i.e., effective frame rate) were adjusted according to the flow rate to normalize the microbubbles' retention time (in terms of frame numbers) and in turn generate a consistent trace. Table II summarizes the CEUS-rendering parameters for three representative flow conditions. Regions where microbubbles were observed to cross path were identified and classified as unstable flow region. On the other hand, regions before the laminar flow layers broke down were categorized to be in stable flow condition. Intermediate boundaries where flow transitioned from laminar to turbulent were also identified for all flow conditions. Regions of interest (ROIs) were selected manually using a Matlab built-in function; the height of the ROI was set to 1.5 mm to match the nozzle diameter. The length of ROIs varied depending on the position of the intermediate boundaries; a 2.5 mm margin was reserved for both stable and unstable zones from the intermediate boundaries as a conservative stance in avoiding ambiguity when selecting ROIs for performance analysis. ROI sizes of each zone for the different flow rates are summarized in the two rightmost columns of Table I.

TABLE II

Contrast-enhanced ultrasound cineloop rendering parameters.

| Flow conditions in Reynolds number Re | Persistence K (Frames) | Overlapping (Frames) | Effective frame rate (fps) |
|---|---|---|---|
| 375 | 240 | 224 | 625 |
| 750 | 120 | 112 | 1250 |
| 1125 | 80 | 74 | 1667 |

Example 2-5: ROC Analysis of Doppler Bandwidth Measurements

To assess DUBI's sensitivity and specificity in determining flow instability, an ROC analysis was conducted. The procedure involved the following key steps. First, the measured Doppler bandwidth estimates within the ROIs for all image frames were classified as either belonging to the stable flow (negative) or unstable flow (positive) groups based on the CEUS reference data. Next, a bandwidth threshold was set to categorize the measured bandwidths to their predicted conditions (stable or unstable); Doppler bandwidth above the threshold was categorized as positive (i.e., unstable) and vice versa. True negative (TN) and false positive (FP) were computed from the stable group, while true positive (TP) and false negative (FN) were counted from the unstable group. This process was repeated at different bandwidth thresholds ranging from 0.1 to 10 kHz with 0.1 kHz increment, and each corresponding set of TN, FN, TP, and FP values was computed. Using these data, the sensitivity [TP/(TP+FN)] and specificity [TN/(TN+FP)] of the test were derived to plot the ROC curve. The area under curve was calculated as a summative measure of the ROC. Also, Youden index (Sensitivity+Specificity−1) was computed for all points on the ROC curve to identify the optimal cutoff that maximizes both sensitivity and specificity with equal weight.

Example 2-5: Comparative Analysis with CFI

The performance of DUBI was contrasted against that for conventional CFI. To facilitate such comparison, CFI frames were computed by applying CFI's scanline-based imaging paradigm to re-process the raw channel-domain datasets that were acquired as described in Example 1-1. Specifically, our platform's GPU beamformer was reconfigured to perform quad-line parallel receive beamforming on each frame of channel-domain data. The full image view was divided into 48 zones, each of which comprised four beams in adjacent lateral positions. Quad-line beamforming was performed over each zone for 10 consecutive pulsing events before advancing to the next zone. Accordingly, at each pixel position in a CFI scanline, the slow-time ensemble was 10 samples in size with 10 kHz sampling rate, yielding an observation period of 10 ms (i.e., same as that for DUBI). The effective CFI frame rate was 20.8 fps. For each slow-time ensemble, tissue clutter was suppressed using a first-order infinite impulse response high-pass filter (0.05 normalized cutoff; with projection initialization), and then mean flow velocity and velocity variance were estimated via Kasai's autocorrelation algorithm. The flow estimates of different pixels in the CFI frame were mapped to a hot-cold hue to render mean flow velocity information. They were also mapped to a tricolor hue to render both mean velocity and variance information.

Example 2-6: Case Demonstration Using Anthropomorphic Phantoms

To further demonstrate the efficacy of DUBI to detect flow instability in a physiologically relevant condition, a series of imaging experiments was conducted on a healthy carotid bifurcation model, a moderately stenosed bifurcation (50% eccentric stenosis relative to the internal carotid artery diameter, as defined based on the NASCET criterion), and a severely stenosed bifurcation (75% eccentric stenosis). These geometries have well-studied flow characteristics as obtained from Doppler ultrasound and particle image velocimetry.

The bifurcation phantoms were fabricated using the same investment casting procedures. The vessel cores (healthy, 50% and 75% eccentric stenosis) were identical to the core geometries previously reported, for which the unstenosed diameters of the common, internal, and external carotid artery branches were 6.0, 4.2, and 3.5 mm, respectively. The vessel cores were first drafted using CAD software (Solid-Works) and were physically fabricated using the FDM system mentioned earlier. The physical builds of the vessel cores were subsequently embedded in PVA solution inside a phantom box (80×295×70 mm$^3$, w×l×h) and three freeze-thaw cycles were administered to solidify the PVA solution. Lastly, the vessel geometries were instated by removing the core (through snapping the core at the bifurcation site and sliding out the snapped parts from both ends).

During experiments, the bifurcation phantoms were connected to the programmable flow pump that was driving a pulsatile flow profile (20 ml/s systolic flow rate; 60 bpm). Plane wave imaging was performed with the transducer surface angled at 20° against the phantom surface using a custom-made PVA coupling wedge. Note that our use of the angled coupling wedge was inspired by another study that used slanted gel pads to generate more favorable beam-flow angles when performing clinical Doppler ultrasound. With this experimental configuration, DUBI cineloops were obtained using the same protocol as described in previous subsections.

Example 3: Findings from Nozzle-Flow Phantom

Example 3-1: DUBI was Effective in Depicting Unstable Flow Regions

Still frames of mean Doppler bandwidth were obtained by averaging over 0.5 s for the three flow conditions. Results are shown in FIGS. 5A to 5C with the intermediate boundary between stable and unstable flow indicated by white arrows (as determined from CEUS). Comparative findings derived from CFI variance mapping (i.e., mean Doppler variance) are also shown in FIGS. 5D to 5F. One general observation to be noted is that, as Re increased from 375 to 750 and 1125, the maximum value in DUBI's mean Doppler bandwidth maps had increased from 2.1 to 3.1 and 5.2 kHz. More importantly, for the Re=1125 case, the development of unstable flow corresponded to a spatial peak zone in the mean Doppler bandwidth maps derived from DUBI. The 5.2 kHz spatial peak value in the unstable flow zone was significantly higher than the spatial maximum of 2.4 Hz in the upstream flow jet near the nozzle. Such visualization was not clearly highlighted in the mean Doppler variance maps, because the upstream flow jet was found to yield similar mean Doppler variance values (spatial maximum: 6.7 kHz) as those in the unstable flow region (spatial maximum: 7.1 kHz).

Example 3-2: DUBI Yielded Similar Findings as CEUS

Figures 6A, 6B, 6C:
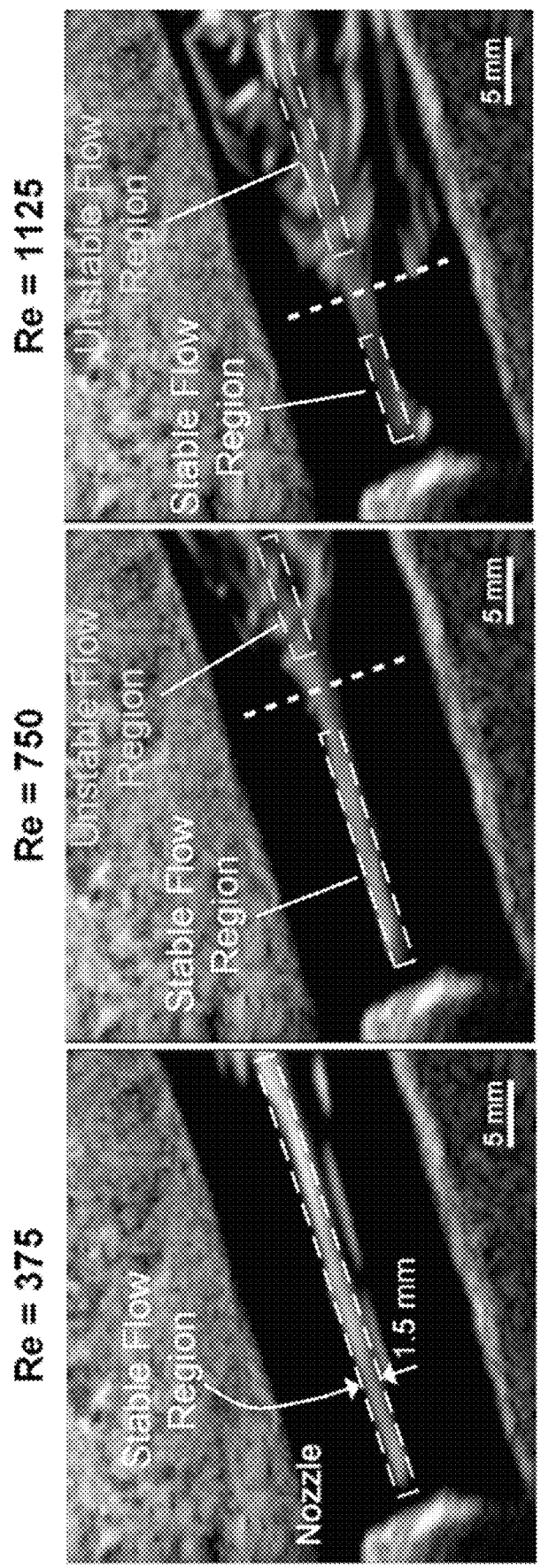
FIGS. 6A-6C are images of a measurement of unstable flow with a contrast enhanced ultrasound (CEUS) method.

As a further analysis, FIGS. 6A to 6C show selected CEUS frames with dashed lines drawn on the figure to indicate the intermediate boundary between stable and unstable flow. The location of these boundaries in the high Re cases (middle and right frames) was found to be in close proximity with the location where a rise in Doppler bandwidth estimate started to appear in FIGS. 5A to 5C, thereby indicating that Doppler bandwidth can be a reliable indicator to discern flow instability.

Example 3-3: DUBI Showed Strong ROC Performance in Mapping Flow Instability

Figure 7A:
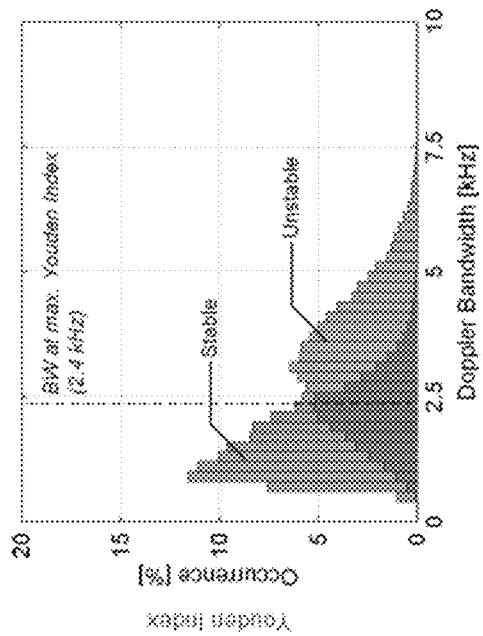
FIGS. 7A-7D are graphs of sensitivity and specificity analysis of a method of detecting flow instability in accordance with some embodiments.
Figure 7B:
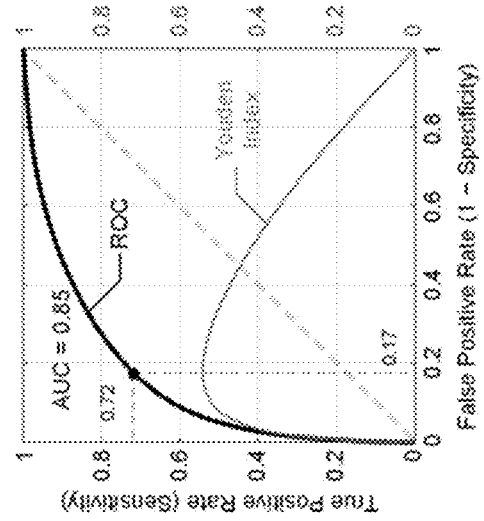
Figure 7C:
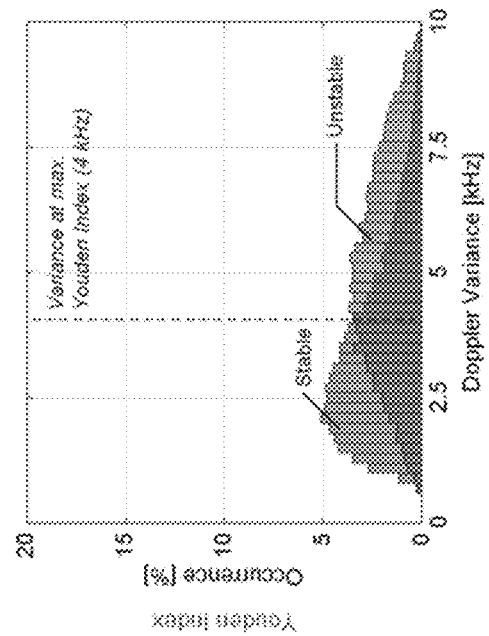
Figure 7D:
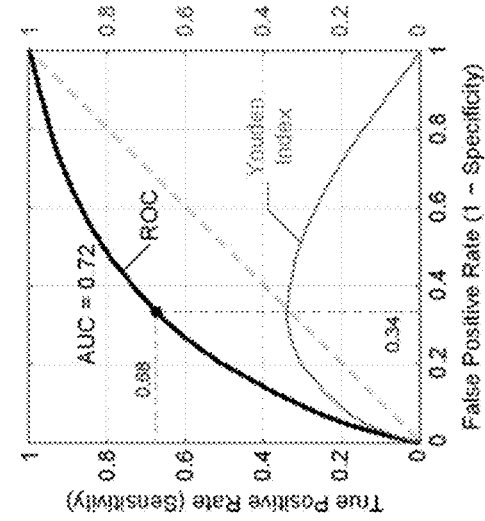

FIG. 7A includes a plot of the ROC curve (dark line) of DUBI with samples collected from all the ROIs at the three flow rates. As can be observed, the ROC curve (with an area under curve of 0.85) was positioned above the diagonal line (gray dashed line), thereby indicating that DUBI has positive predictive power in determining flow instability. The Youden index is also plotted in FIG. 7A (gray line) as a global indicator of sensitivity and specificity. The optimal Youden index was found to be 0.54 when sensitivity and specificity were respectively 0.72 and 0.83. This optimal point corresponded to a bandwidth threshold of 2.4 kHz, as indicated in the bi-population histogram shown in FIG. 7B. These ROC findings represent significant improvements over the ones obtained from Doppler variance mapping. As shown in FIGS. 7C and 7D, the optimal sensitivity and specificity of Doppler variance mapping were 0.68 and 0.66, and they were achieved with a maximum Youden index of 0.34 and a bandwidth threshold of 4.0 kHz. The area under ROC curve for Doppler variance mapping (0.72) was also lower than that for DUBI.

Example 4: Findings from Carotid Bifurcation Experiments

Example 4-1: DUBI Highlighted Unstable Flow Emerging from Stenosis Site

When DUBI was applied to pulsatile carotid bifurcation phantoms, it was found to capable of highlighting flow instability that arises downstream from the stenosis site in diseased bifurcations.

An observation to be noted is that the range of Doppler bandwidths increased in the stenosed vessel (upper branch) because of the lumen narrowing at the stenosis site. This observation was consistent with our findings from the flow nozzle model, whereby an increasing Re would result in greater Doppler bandwidth (in the bifurcation experiments, the flow profile remained unchanged but the "nozzles" were narrower as stenosis increased). Doppler bandwidths in the healthy model were low (<1.4 kHz) throughout the entire cardiac cycle. In contrast, high Doppler bandwidths (>2.4 kHz) were observed in both diseased models, especially at the flow jet region during flow systole and the dicrotic wave phase of the cardiac cycle.

Selected frames of DUBI are shown in FIGS. 8A to 8O to facilitate further interpretation of the information provided by DUBI at specific time points of interest. This figure depicts frames from peak systole (FIGS. 8A, 8F, and 8K), at the instant with peak Doppler bandwidth measured in a cardiac cycle (FIGS. 8B, 8G, and 8I), end systole (FIGS. 8C, 8H, and 8M), end diastole (FIGS. 8D, 8I, and 8N), and the corresponding Doppler spectrogram at the stenosis site (FIGS. 8E, 8J, and 8O). Three main observations can be made. First, the maximum Doppler bandwidth increased as the degree of stenosis increased, as reflected by the brighter thermal hue in DUBI frames. Second, the peak Doppler bandwidth was found at the jet tails [FIGS. 8K and 8L] where flow perturbations were strongest. Third, for the 50% stenosis model (FIGS. 8F to 8J), significant increase in Doppler bandwidth was only found during flow systole, whereas for the 75% stenosis model, its high-range Doppler bandwidth sustained throughout the entire cardiac cycle (FIGS. 8K to 8O). The timing and positions of peak Doppler bandwidth were in general consistent with those measured using turbulence intensity under similar flow conditions as previously reported.

Example 4-2: Maximum Doppler Bandwidth is Correlated with Degree of Stenosis

As a further analysis of DUBI, FIGS. 9A and 9B show time traces of the measured Doppler bandwidths at the stenotic jet area (dark line) and its tail (gray line) for the two diseased bifurcation phantoms. A dash line to indicate peak systole is also included in this figure. For the 75% stenosis model, the maximum Doppler bandwidth at the jet tail was significantly higher (7.7 kHz) compared to that for the 50% stenosis model (3.3 kHz). Also, the Doppler bandwidth at the jet tail in the 75% stenosis model shows greater temporal fluctuation over the cardiac cycle, and it expectedly showed a decreasing trend during end systole (100 ms after peak systole) since flow deceleration naturally favored reestablishment of stable flow conditions. Another point worth noting is that in both diseased models, the Doppler bandwidth at the flow jet was lower than that at the jet tail. This finding expectedly indicates that flow instability mainly emerged not at the flow jet, but downstream from the jet. For the 75% stenosis model, at the stenotic flow jet, Doppler bandwidth was found to show a greater extent of fluctuation. This trend is likely because the higher temporal variation in jet speed for the 75% stenosis model naturally favors transitioning between stable and unstable flow regimes.

Example 5: DUBI as a Framework for Mapping Flow Instability

Visualizing unstable flow noninvasively is not a trivial task. In particular, two practical flow characteristics must be addressed when devising a new flow instability mapping framework: (a) at a given time instant, unstable flow pattern may vary spatially because of its dissipative nature; (b) over a cardiac cycle, flow conditions may vary temporally due to the pulsatile nature of blood flow. DUBI has been specifically designed to visualize and track these spatiotemporal dynamics. It is equipped with three key features that have collectively enabled visualization of unstable flow. First, DUBI is able to track spatial variations in flow instability (via local Doppler bandwidth measurements) over the entire image view at high-frame-rates beyond the video display range [FIG. 3A]. Second, DUBI uses an AR modeling approach to consistently derive Doppler bandwidth estimates [FIG. 3B]. Third, DUBI's triplex display approach enables simultaneous visualization of flow instability information (Doppler bandwidth), flow trajectory (flow speckles), and the anatomical background [FIG. 3C].

DUBI's efficacy in identifying unstable flow for a series of flow conditions ranging from laminar to turbulent flow is demonstrated at least in FIGS. 4A and 4B. The performance of DUBI was first evaluated on a nozzle-flow setup (FIGS. 4A and 4B) with CEUS images acquired as benchmarking references (FIGS. 6A to 6C). Unstable flow regions were found to correspond to high Doppler bandwidth regions in DUBI (FIGS. 5A to 5C). Such correspondence was broadly found to be sensitive and specific in comparison to conventional CFI mapping of Doppler variance (FIGS. 7A to 7D). The practical merit of DUBI was also established through a series of carotid bifurcation experiments (FIGS. 8A to 8O). DUBI was found to be effective in identifying unstable flow at the jet tail downstream from a stenosis site (FIGS. 9A and 9B).

DUBI represents the first image-based, noninvasive flow instability mapping framework with fine temporal resolution. From a clinical diagnosis standpoint, this framework unlocks new potentials in improving atherosclerotic disease management. For example, emergence of unstable flow can indicate the onset of plaque formation, so DUBI may help facilitate early diagnosis of atherosclerosis. In addition, new insights on plaque progression may be obtained in correlation with the intensity and size of flow instability zones, since unstable flow has been shown to contribute to the progression of an atherosclerotic plaque. Moreover, given that our nozzle-flow setup has demonstrated initial potential in detecting flow instability emerging from a stenosed flow outlet, DUBI may be further developed as a new tool in valvular stenosis diagnostics to complement other emerging ultrasound techniques.

Example 6: GPU-Based Implementation of Burg's Method

For our GPU computing kernel for Doppler bandwidth estimation, a thread block was allocated to handle the estimation of Doppler bandwidth for the slow-time ensemble of one pixel in the DUBI frame. Note that the corresponding slow-time ensemble x[n] was first transferred to the shared memory of the GPU for fast data access. The thread block, containing N threads (i.e., same as the slow-time ensemble size), then proceeded to derive the set of $P^{th}$-order AR parameter values for that slow-time ensemble by executing a fast implementation of Burg's method that involved P iterations from p=1 to p=P. Within each iteration, two computational steps were carried out. First, the compute threads were tasked to calculate the forward and backward prediction error ensembles, respectively denoted as $e^f_p[n]$ and $e^b_p[n]$. Specifically, for the $p^{th}$ iteration, the nth thread was tasked to compute the nth sample in the following error ensemble (each with N samples):

$$e^f_p[n] = x[n] + \sum_{k=1}^{p} a_{P,k} x[n-k] \quad (A1)$$

$$e^b_p[n] = x[n] + \sum_{k=1}^{p} a_{P,k} x[n-p+k] \quad (A2)$$

Note that the mean of (A1) and (A2) corresponded to the error term e[n] in the AR model stated in (1) for the $p^{th}$ iteration.

In the second computational step of the same iteration, a sub group of threads were tasked to compute the intermediate AR parameters $a_{p,k}$. The second computational step achieved the intermediate AR parameters by updating the intermediate AR parameters using the following equations:

$$a_{p,i} = a_{p-1,i} + \varphi_p a^*_{p-1,p-i} \quad (A3)$$

where i=1, 2, . . . , p–1, $a_{0,0}$=1, * denotes complex conjugate, and $$a_{p,p} = \varphi_p \quad (A4)$$

$$\varphi_p = \frac{-2\sum_{n=p}^{N-1} e^f_{p-1}[n] e^{b*}_{p-1}[n-1]}{\sum_{n=p}^{N-1} \left(|e^f_{p-1}[n-1]|^2 + |e^b_{p-1}[n-1]|^2\right)} \quad (A5)$$

The set of AR model coefficients was finalized after repeating the above computational steps for P iterations.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of detecting flow instability, comprising:
   insonating an area of interest with ultrasound wave pulses;
   acquiring radio frequency (RF) data from echo pulses of the ultrasound wave pulses;
   processing the RF data; and
   deriving a Doppler band-width from the processed RF data using autoregressive (AR) modeling,
   comparing the Doppler band-width at multiple pixels concurrently of a full-view image of the area of interest with a predetermined value;
   detecting a flow instability in response to a Doppler band-width equal to or larger than the predetermined value;
   detecting a stable flow in response to a Doppler band-width smaller than the predetermined value; and
   displaying a color image, wherein the color image includes a first color indicating the flow instability and a second color indicating the stable flow,
   wherein the flow instability and the stable flow are detected without discarding any obtained Doppler band-width data at the multiple pixels.

2. The method of claim 1, wherein the ultrasound wave pulses comprise at least one selected from an unfocused plane wave, a diverging spherical wave, a weakly focused wide beam wave and a focused converging wave.

3. The method of claim 1, wherein processing the RF data comprises beamforming the RF data to generate the full-view image of the area of interest.

4. The method of claim 3, wherein processing the RF data further comprises performing slow-time sampling for all pixels within the full-view image.

5. The method of claim 3, wherein processing the RF data further comprises:
   forming a 3D data matrix by stacking a plurality of the full-view images along a slow-time dimension; and
   applying clutter filtering to the 3D data matrix.

6. The method of claim 1, wherein deriving the Doppler band-width of the processed RF data using AR modeling comprises: modeling an $n^{th}$ sample in a slow-time ensemble with N samples according to a $P^{th}$-order complex AR model representation according to the following Equation 1:

$$x[n] = -\sum_{k=1}^{P} a_{P,k} x[n-k] + e[n] \quad \text{<Equation 1>}$$

wherein in Equation 1, $a_{P,k}$ is the $k^{th}$ complex AR parameter of the model, and e[n] is the nth sample in the complex modeling error.

7. The method of claim 6, wherein deriving the Doppler band-width of the processed RF data using AR modeling further comprises calculating Doppler power spectrum $S_{AR}$[f] for the ensemble x[n] is constructed from the AR model through parametric spectral fitting as defined by the following Equation 2:

$$S_{AR}[f] = \frac{\sigma_p^2 \Delta t}{\left|1 + \sum_{k=1}^{P} a_{P,k} e^{-j2\pi f k \Delta t}\right|^2} \qquad \text{<Equation 2>}$$

wherein, in Equation 2, f is the bin frequency, $\Delta t$ is the pulse repetition interval and $\sigma_p^2$ is an average of mean powers of forward and backward prediction errors.

8. The method of claim 1, wherein deriving the Doppler band-width comprises estimating the Doppler band-width over a time window of 50 ms or less.

9. The method of claim 1, further comprises displaying a map of the Doppler band-width in synchronize with a flow speckle pattern revealing the flow trajectory or a B-mode image.

10. The method of claim 1, wherein detecting the flow instability comprises detecting blood flow instability in a blood vessel of a human or an animal.

11. The method of claim 10, wherein detecting the flow instability comprises detecting blood flow instability caused by carotid atherosclerotic stenosis.

12. A device for detecting flow instability, comprising:
a display;
an emitter configured to insonate ultrasound wave pulses on an area of interest;
a receiver configured receive echo pulses of the ultrasound wave pulses;
a scanner configured to acquiring radio frequency (RF) data from the echo pulses;
a processor configured to:
process the RF data;
derive a Doppler band-width from the processed RF data using autoregressive (AR) modeling;
compare the Doppler band-width at multiple pixels concurrently of a full-view image of the area of interest with a predetermined value;
detect a flow instability in response to a Doppler band-width equal to or larger than the predetermined value;
detect a stable flow in response to a Doppler band-width smaller than the predetermined value; and
instruct the display to display a color image, wherein the color image includes a first color indicating the flow instability and a second color indicating the stable flow,
wherein the flow instability and the stable flow are detected without discarding any obtained Doppler band-width data at the multiple pixels.

13. The device of claim 12, wherein at least one of the emitter or the receiver comprises an ultrasound array transducer.

14. The device of claim 12, wherein the processor is configured to process the RF data by beamforming the RF data acquired by the receiver to generate the full-view image of the area of interest.

15. The method of claim 14, wherein the processor is further configured to process the RF data by performing slow-time sampling for all pixels within the full-view image.

16. The device of claim 12, wherein the processor is configured to derive the Doppler band-width by modeling an $n^{th}$ sample in a slow-time ensemble with N samples according to a $P^{th}$ order complex AR model representation according to the following Equation 1:

$$x[n] = -\sum_{k=1}^{P} a_{P,k} x[n-k] + e[n] \qquad \text{<Equation 1>}$$

wherein in Equation 1, $a_{P,k}$ is the $k^{th}$ complex AR parameter of me model, and e[n] is the nth sample in the complex modeling error.

17. The device of claim 12, wherein the processor is configured to derive the Doppler band-width by calculating Doppler power spectrum $S_{AR}[f]$ for the ensemble x[n] is constructed from the AR model through parametric spectral fitting as defined by the following Equation 2:

$$S_{AR}[f] = \frac{\sigma_p^2 \Delta t}{\left|1 + \sum_{k=1}^{P} a_{P,k} e^{-j2\pi f k \Delta t}\right|^2} \qquad \text{<Equation 2>}$$

wherein, in Equation 2, f is the bin frequency, $\Delta t$ is the pulse repetition interval and $\sigma_p^2$ is an average of mean powers of forward and backward prediction errors.

18. The device of claim 12, wherein the processor is further configured to generate a flow speckle pattern revealing the flow trajectory or a B-mode image using the RF data acquired by the receiver.

19. The device of claim 18, wherein the processor is further configured to generate a map of the Doppler band-width, and to display the map in synchronize with the flow speckle pattern or the B-mode image.

* * * * *